United States Patent
Jaschul et al.

(10) Patent No.: US 8,947,660 B2
(45) Date of Patent: Feb. 3, 2015

(54) METHOD AND DEVICE FOR CARRYING OUT AN OPTICAL COMPARISON BETWEEN AT LEAST TWO SAMPLES, PREFERABLY BY COMPARING SECTIONS THAT CAN BE SELECTED

(75) Inventors: Johannes Jaschul, Germering (DE); Martin Kosina, Stephanskirchen (DE); Kai Rainer Hummel, Rosenheim (DE)

(73) Assignee: Schattdecor AG, Thansau (DE)

( * ) Notice: Subject to any disclaimer, the term of this patent is extended or adjusted under 35 U.S.C. 154(b) by 528 days.

(21) Appl. No.: 13/318,294

(22) PCT Filed: Apr. 29, 2010

(86) PCT No.: PCT/EP2010/002642
§ 371 (c)(1),
(2), (4) Date: Dec. 27, 2011

(87) PCT Pub. No.: WO2010/124866
PCT Pub. Date: Nov. 4, 2010

(65) Prior Publication Data
US 2012/0105860 A1    May 3, 2012

(30) Foreign Application Priority Data
Apr. 30, 2009 (DE) .......................... 10 2009 019 545

(51) Int. Cl.
*G01J 3/30* (2006.01)
*G01J 3/10* (2006.01)
(Continued)

(52) U.S. Cl.
CPC .... *G01J 3/10* (2013.01); *G01J 1/04* (2013.01); *G01J 3/0251* (2013.01);
(Continued)

(58) Field of Classification Search
CPC .................................... G01J 3/45; G01J 3/457
USPC .......................... 356/303, 305, 306, 326, 328
See application file for complete search history.

(56) References Cited

U.S. PATENT DOCUMENTS

| | | | | |
|---|---|---|---|---|
| 5,412,578 A | * | 5/1995 | Takagi et al. ................. | 700/192 |
| 6,078,398 A | * | 6/2000 | Feldman et al. .............. | 356/402 |
| 2002/0006233 A1 | * | 1/2002 | Adachi et al. ................. | 382/289 |
| 2003/0011767 A1 | | 1/2003 | Imura et al. | |

(Continued)

FOREIGN PATENT DOCUMENTS

| | | |
|---|---|---|
| EP | 0 586 708 A1 | 3/1994 |
| EP | 1 041 378 A1 | 4/2000 |

(Continued)

OTHER PUBLICATIONS

International Search Report for PCT/EP2010/002642, mailed Jul. 23, 2010.

*Primary Examiner* — Jonathan Hansen
(74) *Attorney, Agent, or Firm* — Nixon & Vanderhye P.C.

(57) ABSTRACT

An improved method and an improved device for carrying out an optical comparison between at least two samples, preferably by comparing sections that can be selected, is characterized by the following characteristics: the sample (UR, LE, I) that is to be examined and is characterized by a non-uniformity in the structure and/or color is illuminated by diffused light; from the light reflected by the sample (UR, LE, I) to be examined, an interference spectrum is created by means of a spectrometer; the interference spectrum created by the spectrometer is depicted on a camera; the interference spectrum obtained in this way and/or values of the sample (I) to be examined derived therefrom are used as sample values which are compared to sample values of a reference sample (UR, LE) obtained accordingly.

22 Claims, 5 Drawing Sheets

(51) Int. Cl.
*G01J 1/04* (2006.01)
*G01J 3/02* (2006.01)
*G01N 21/47* (2006.01)
*G01N 21/898* (2006.01)
*G01N 21/956* (2006.01)

(52) U.S. Cl.
CPC ............. *G01J 3/0254* (2013.01); *G01N 21/474* (2013.01); *G01N 21/8983* (2013.01); *G01N 21/95607* (2013.01)
USPC ........................................................ 356/306

(56) References Cited

U.S. PATENT DOCUMENTS

2006/0012782 A1\* 1/2006 Lim et al. ................... 356/237.5
2006/0161788 A1   7/2006 Turpin et al.
2007/0086009 A1\* 4/2007 Ehbets et al. ................. 356/402

FOREIGN PATENT DOCUMENTS

WO   WO2004/090488   10/2004
WO   WO 2008/034156   3/2008

\* cited by examiner

METHOD AND DEVICE FOR CARRYING OUT AN OPTICAL COMPARISON BETWEEN AT LEAST TWO SAMPLES, PREFERABLY BY COMPARING SECTIONS THAT CAN BE SELECTED

The invention relates to a method and device for carrying out an optical comparison between at least two samples, preferably by comparing sections that can be selected, according to the preambles of claims 1 and 14 respectively.

Various methods and devices have already been made known for comparing single-colour colour samples, for example by RAL identification.

In addition, however, many applications are also in principle known in which the samples which are to be compared have an inconsistent structure or an inconsistent colour.

Problems of this type occur for example when printing what are known as decor papers for producing decorative surfaces. These printed decor papers are used inter a/ia for reproducing a wide range of wood decors which have differently coloured grains, which generally stand out clearly as darker-coloured lines against a lighter background, as well as different shades and colourations. However, the above-mentioned configurations also apply equally to fantasy decors. When printing decors of this type, repeats are often printed at large time intervals, for example for a new customer order. In this context, the decor of the order which is to be reprinted has to correspond exactly to the original sample, i.e. to the original print, which is also sometimes referred to in the following as the reference print for the relevant decor. An original sample is generally established together with the customer and is the reference for the colour and the printout quality of the respective decor.

If a decor is printed in repeats relatively frequently, then the current print (sometimes also referred to in the following as the current sample I), in addition to the original sample, is also further compared with a representative sample from the last previous print order, i.e. with what is known as an LE sample, specifically the "last-delivery" sample. Like the original sample, the last-delivery sample is also a further reference for the colour and printout quality of the decor. This means that in a new print order, the colour and printout quality of the last-delivery decor should also be achieved as optically exactly as possible.

In particular for printing decor paper, no automated comparison method which is satisfactory overall has been made known thus far.

A method for comparing the similarity of articles or of digital object images taken of two articles, in particular an actual image and a target image of the article, using statistical methods, is known for example from AT 504 213 B1.

This prior publication proposes a camera-based system with which an actual image, for example of a decor section which is to be tested, is compared with a target image which forms the reference value. The method can thus be referred to as a pixel-orientated method.

For this purpose, the statistical distribution of the intensities of the individual pixels and/or of given pixel regions is determined for a coincident image region, and by means of the statistical distributions, obtained therefrom (using statistical methods), of the intensities, it is tested whether the extent of the similarity of the two statistical distributions of the intensities can be used as a measure of the similarity of the two article images.

In this case, the statistical distribution of the intensities is determined for a particular colour channel or wavelength regions for the target image, so as subsequently to compare these target values with the values of the actual image, which were determined previously by the same method.

The colour channels of a hyperspectral digital colour image comprise many wavelengths in which the image has been captured. Therefore, the aforementioned prior publication offers the basic solution of using the colour channels red, green and blue for the evaluation. Therefore, according to the prior publication, two image sets for the actual image are compared with the target image for the colour channels RGB (i.e. red, green, blue) so as subsequently to evaluate the intensity distribution by the statistical methods and to establish whether or not the two images captured using a camera are similar. In principle, the individual sets of images could also be broken up as hyperspectral images in a predetermined wavelength range, in particular between 360 nm and 830 nm. However, this is merely a theoretical possibility, since thus far no camera systems are known with which hyperspectral images of this type could be produced. In addition, this would have the consequence, as is stated in the prior publication, that when image sets of this type are present, as regards hyperspectral images, the individual images of each image set have to be compared with one another so as to make a corresponding assertion as regards the similarity of the images which are to be compared. A further difficulty is that the statistical distribution of the determined intensities has to be determined in relation to the individual pixels and/or the individual predetermined pixel regions.

It is also a drawback of the prior art that for the image sets which comprise hyperspectral images and/or a corresponding number of colour channels, it is always necessary for the mutually corresponding images to correspond not only as regards the image regions, but also as regards the wavelength ranges. Otherwise, it is not possible to make adequate assertions.

A further drawback is that to carry out a comparison with a previously calibrated sample, the images which are to be compared or which are to correspond of a sample which is currently to be tested have to be of the same spatial resolution. Otherwise, a corresponding conversion of the image coordinates would be necessary so as to be able to compare coincident image regions in the images which are to be compared or which are to correspond.

By contrast, the object of the present invention is to carry out, with comparatively simple means, a high-precision analysis and thus a high-precision comparison between at least two samples of a decor, which is in particular unevenly coloured and/or structured in itself, in particular on two or more identical decor sections, and as a function thereof to make a reliable assertion as to whether the tested sections can be denoted as highly similar or identical based on the colouring and/or the structure.

The object is achieved for the method in accordance with the features given in claim 1 and for the device in accordance with the features given in claim 15. Advantageous configurations of the invention are given in the dependent claims.

It must be considered extremely surprising that it is possible in the context of the invention, with comparatively simple measures and with a method with can also be carried out temporally rapidly, to make high-precision assertions as regards the similarity of at least two samples which are to be compared, in particular on a plurality of decor sections which are to be compared.

In this context, the invention follows a different path from the prior art.

Whilst the prior art, in particular including the aforementioned category-defining prior publication, starts from a pixel-based method, i.e. an image-producing method, in which images of the samples or sections which are to be compared are captured using a camera system, the invention by contrast proposes an integral solution method.

According to the invention, for the overall evaluation of a sample which is to be analysed, in general a decor section which is to be analysed (i.e. merely a small sub-region of an overall sample) will be used, this decor section being illuminated with diffuse, i.e. scattered light. The light reflected by the sample which is to be analysed is preferably bundled and imaged onto a sensor by means of a spectrometer, preferably using a diffraction grating. This sensor may for example be a matrix or line-scan camera, for example what is known as a CCD or CMOS camera, etc.

Using an integral measurement device of this type, an interference spectrum can thus be determined for the section which is to be analysed, and can be digitalised accordingly by evaluation electronics downstream from the sensor camera. The end result is a magnitude spectrum, i.e. an intensity distribution (amplitude distribution) over the wavelength (or over the frequency).

Thus, in the context of the invention it is easily possible, in a single step, to achieve a high resolution for the determined data, for example a resolution of approximately 10 nm, in general for example from 1 nm to 20 nm, or the like. The magnitude spectrum obtained according to the invention over the wavelength-dependent intensity distribution subsequently results, for example at a length of 400 nm, in 256 values, which can also be referred to as sampling points for the obtained information. These then have a resolution of approximately 1.56 nm.

These data are subsequently processed further in a digitalised form, so as ultimately to determine a derived characteristic value which can be compared with a correspondingly determined characteristic value of a reference section.

In the context of the invention, an improved method is additionally proposed so as to calibrate exactly the same section, in a sample which is newly to be tested, as was evaluated previously in a previously calibrated reference sample.

In a preferred embodiment of the invention, this can be carried out with an additionally provided camera which explicitly detects one, two, three or more decor sections, in the sample which is to be tested, which correspond to the identically determined reference sections which were used in the image detection of the original or LE sample. By cross-fading the reference decor section with the visible decor section produced by the additionally provided camera for the sample I which is currently to be tested, it can subsequently be established directly whether the two pictures are coincident or whether differences can still be identified. In this context, the sample which is to be calibrated is preferably located on a measuring table which can be adjusted in two mutually perpendicular directions, and which can subsequently be displaced in such a way that the reference image and the actual image are completely identical as regards the decor section which is to be calibrated. Ultimately, this manual adjustment can also be carried out by known automated methods by means of the cross-faded images.

In the following, the invention is explained further by way of drawings, in which, in detail:

Figure 1:
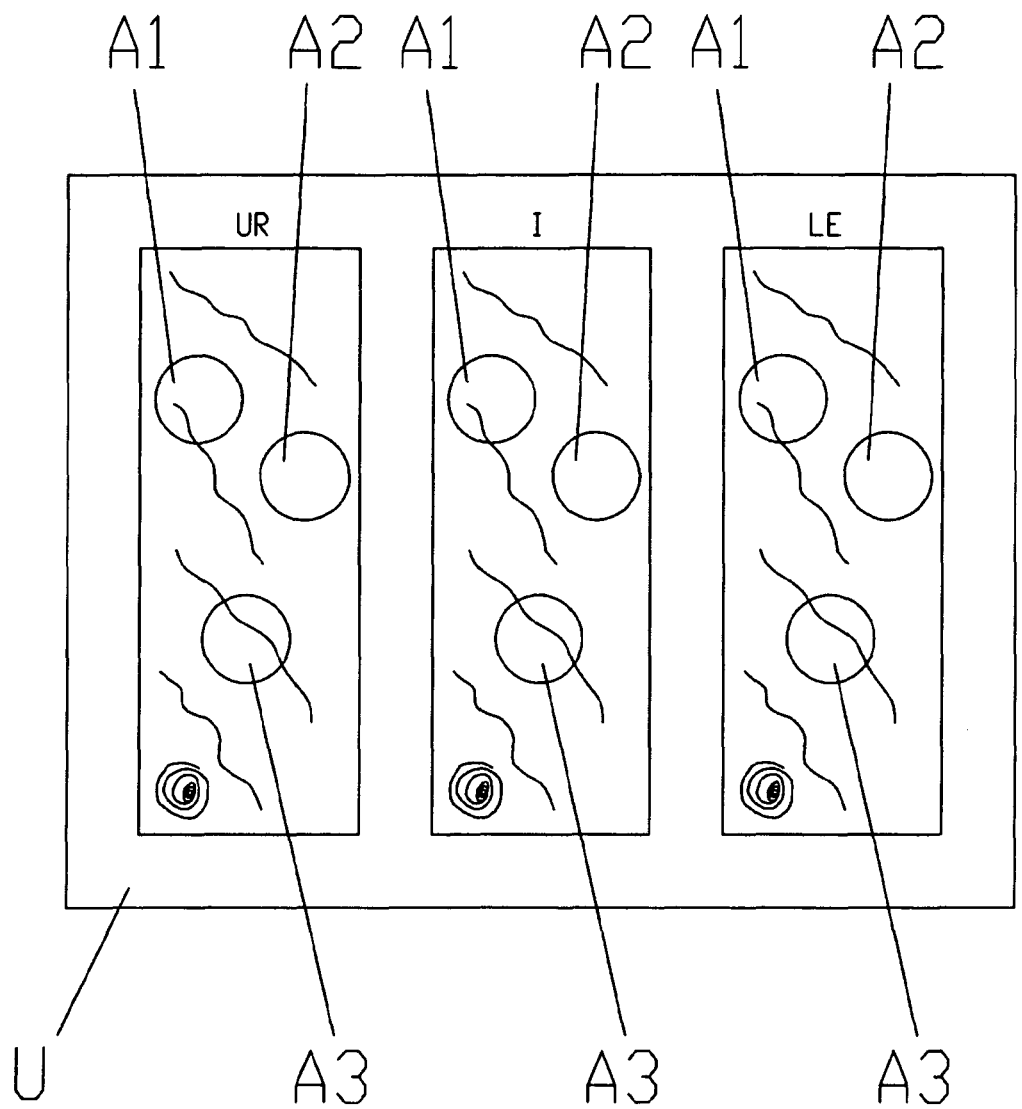
FIG. 1 is a schematic plan view of three different samples of the same decor.

FIG. 1 schematically reproduces three samples of the same decor, specifically the example of an original sample, a reference sample LE (this being what is known as the last-delivery sample) most recently printed based on the original sample, and a new current sample I which is currently being printed or is to be printed, which are intended to provide examples of three samples UR, LE and I, and for example the current sample I is to be compared for identity with the most recently printed sample LE or the original sample UR.

The aforementioned UR, LE and I samples are for example positioned, fixed, glued etc. to a flat base. The samples can thus also be impregnated or lacquered and laminated on a base (a substrate).

For each of the three samples, one, two or a plurality of decor sections A1, A2, A3 etc. can be established which are typical of a decor of this type, which is inconsistent in structure and colour.

By means of these sections A1, A2, A3 etc., it is ultimately to be compared whether the order which is currently to be printed, i.e. the current sample I, is identical with the most recently printed sample LE or with the original sample UR. For this purpose, the following explains how to detect for example the data of a reference sample, which are obtained from decor sections and are subsequently to be used as a basis for the sample which is to be tested and measured and which is currently to be printed.

Figure 2:
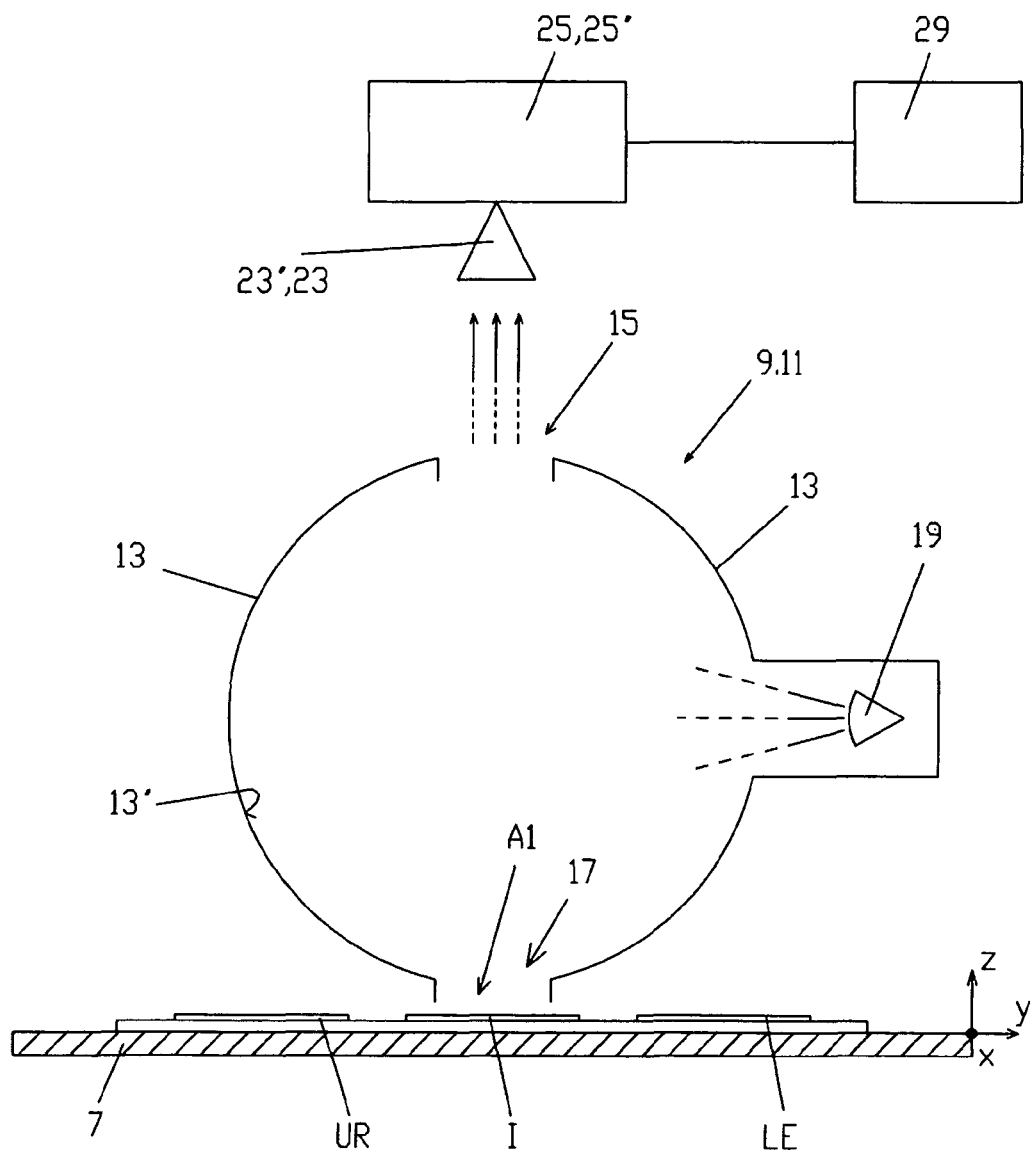
FIG. 2 is a schematic axial cross-section through a colour spectrum measurement device.

A corresponding device constructed according to the invention is shown in a schematic axial sectional drawing in FIG. 2.

FIG. 2 shows by way of example a table, referred to in the following as a measuring table 7, which can be displaced in the X-Y direction (the X direction extending perpendicular to the Y-direction which is shown by a line in FIG. 2) and on which for example one or all of the aforementioned samples UR, LE and I are located.

The measuring device 9 is arranged directly on top of these samples or at a small spatial distance therefrom (the distance may for example be only a few millimeters). As an alternative to the displacement of the measuring table in the X and Y directions, it is also sufficient for the measuring device 9 to be displaceable in the X and Y directions. This device is preferably at least also displaceable along the Z axis perpendicular thereto, so as to align the device correspondingly close above the sample.

In the embodiment shown, the measuring device 9 comprises what is known as an Ulbricht sphere 11. The Ulbricht sphere is a component such as may be used in optical technology. In this case, the Ulbricht sphere serves in particular to produce diffuse radiation, i.e. scattered radiation, which can be produced from directed radiation.

According to the embodiment, it can be seen that the Ulbricht sphere 11 comprises a spherical housing 13, which generally consists of two hemispheres which can be joined together along an equator. Inside the spherical housing 13, the internal wall 13' of the spherical housing 13 is coated and/or formed so as to be diffusely reflective.

In the embodiment shown, the Ulbricht sphere 11 comprises a measuring port 15, positioned further upwards, and diametrically opposite, underneath in the embodiment shown, a light exit port 17. A radiation cell 19 (which generally does not yet produce diffuse radiation) is arranged at a right angle to this axis and radiates light into the interior of the Ulbricht sphere.

Since the internal coating provided on the internal wall 13' is generally formed from highly diffusely reflective materials (white in colour), the internal surface of the Ulbricht sphere produces virtually ideally diffusely scattered radiation. This virtually ideally diffuse radiation is also produced in that the diameter of the measuring port, the light exit port and the port of the radiation source 19 is considerably smaller than the internal diameter of the Ulbricht sphere, in such a way that only light which has previously been reflected repeatedly on the internal surface can reach the exit level 17. Therefore, if possible, the area of all of the ports inside the Ulbricht sphere should not exceed 5% of the total surface area.

This diffuse radiation also exits inter alia through the light exit port 17 positioned below, where it impinges on the decor section A1, A2 or for example A3 which is to be calibrated and evaluated on one of the samples UR, LE or I.

The diffuse light reflected from the sample which is to be tested or the section of UR LE or I which is to be tested can escape through the Ulbricht sphere, at least in part through the light exit port 15 positioned above.

As can also be seen from FIG. 2, a spectrometer 23 is provided outside the Ulbricht sphere 11 in the beam path of the light reflected from the sample which is to be tested. The spectrometer 23 makes it possible to resolve the light spectrum in such a way that an intensity distribution is obtained as a function of the wavelength and thus of the frequency of the different light components (light channels).

In principle, any suitable spectrometers can be used as a spectrometer. For example the use of a prism as a spectrometer is known. In the embodiment shown, however, a diffraction grating is preferably used which is formed so as to result in a resolution, of the interference spectrum to be obtained of the light reflected from the sample, of approximately 1 nm to 20 nm, preferably a resolution of <15 nm, <14 nm, <13 nm, <12 nm, <11 nm, <10 nm, <9 nm, <8 nm, <7 nm, <6 nm, <5 nm, <4 nm, <3 nm or <2 nm.

This interference spectrum obtained by way of the spectrometer 23, which is preferably in the form of the diffraction grating 23', is subsequently imaged onto a camera 25, for example a CCD camera, i.e. what is known as a CCD sensor 25'. As is known, a CCD sensor is an optical sensor, which is for example based on charge-coupled device technology. Equally, this may also preferably be a CMOS camera.

Therefore, a matrix or line-scan sensor can be used, since unlike in the prior art, rather than a pixel-orientated image of the sample which is to be analysed, an integral light spectrum is recorded, such as is produced for example by a diffraction grating.

Figure 3:
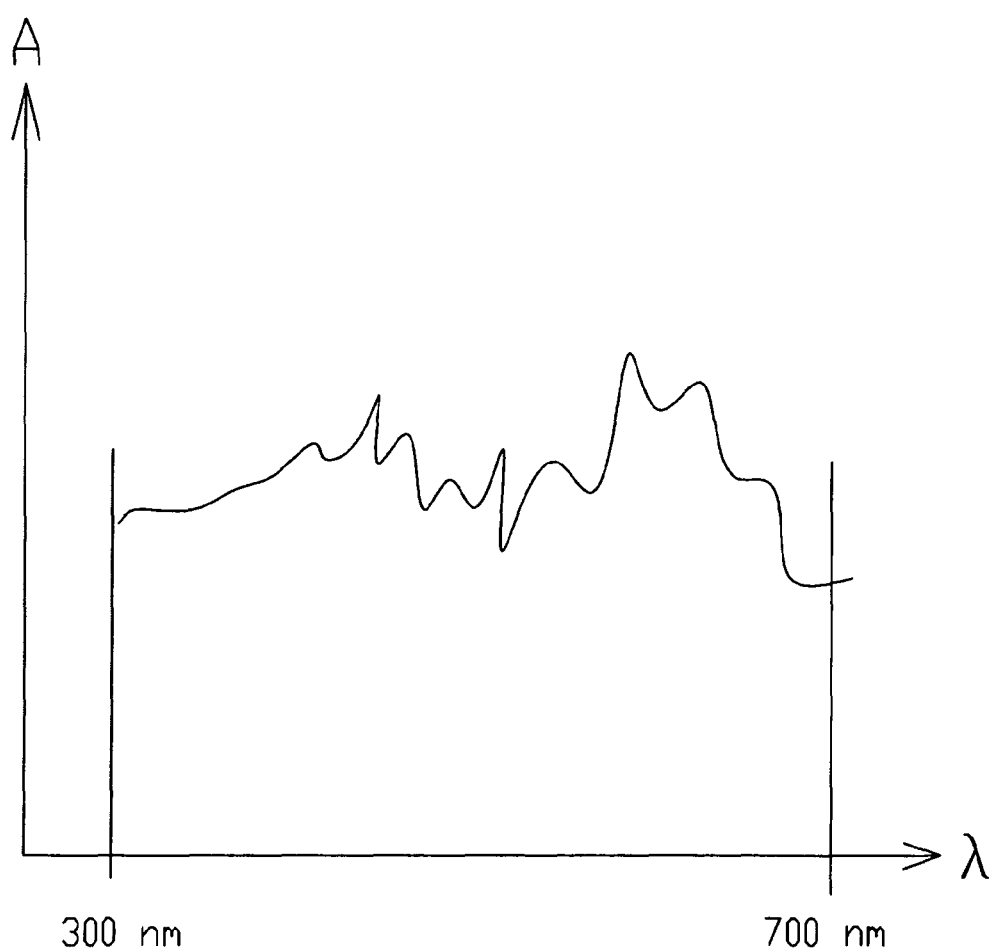
FIG. 3 is an example of an obtained spectrum.

FIG. 3 shows by way of example the result of a light spectrum of this type in which for example the intensity or amplitude A is reproduced on the Y axis against the light wavelength A or the light frequency f. In the embodiment according to FIG. 3, a range of 300 nm to 700 nm for example is taken into account, i.e. a light wavelength range of for example 400 nm, which results in for example 256 sampling points at a resolution of approximately 1.56 nm, depending on the selected diffraction grating. The amplitude interference spectrum should thus preferably have a resolution of <20 nm, in particular of <15 nm, <14 nm, <13 nm, <12 nm, <11 nm, <10 nm, <9 nm, <8 nm, <7 nm, <6 nm, <5 nm, <4 nm, <3 nm, or <2 nm.

This measurement result, shown in FIG. 3 as a diagram or measurement curve, comprises precise items of information as to the structure and/or the colour of the analysed decor section and thus of the analysed section. If the spectral intensity values shown in FIG. 3 have been determined from a reference sample, these data are stored and preferably serve as reference values from then on.

In principle, corresponding values are subsequently determined in the same manner from a new sample which is to be tested in relation to an identical decor section, and the values thus detected (similarly to in FIG. 3) are subsequently compared with the previously determined values of the reference print sample so as to establish, as a function of the diagrams to be compared according to FIG. 3, whether or not the samples which are to be compared of a decor, which is formed inconsistently in structure and colour, are the same or identical in overall colour impression.

What is surprising is that with the integral evaluation, taking into account the interference spectrum, it is possible to make a reliable assertion as to whether or not two or more samples which are to be compared are identical, even though the structure provided in the same respective section of the decor may in itself have different colour ranges or colour nuances, including the wood grain and the line structures.

Finally, FIG. 2 also further shows an evaluation means 29, generally either an electronic means comprising a microprocessor or a computer, in which the spectral values shown in FIG. 3 of various samples are compared with one another so as to decide whether the samples are the same or different from one another. Rather than using the spectral values themselves for the decision as to whether or not the samples are identical, it would also be possible to use evaluation values such as Lab values or Labch values, which correspond to human colour perception. In this context, there are no restrictions to particular methods or evaluation criteria. By way of this comparison, it can subsequently be reliably established whether or not the two or more samples which are to be compared can be denoted as identical or virtually identical.

Finally, these values can also be represented graphically, specifically on a display means or a display. Equally, these values can also be printed out, including resulting instructions as to how the colour recipe is to be changed to achieve the desired colour impression, in such a way that the samples which are to be compared, in the embodiment shown the decor which is to be compared, can actually be denoted as identical.

As explained previously, a sufficiently precise comparison and a precise evaluation as to whether two samples which are to be compared are actually identical or not are only possible if the same decor sections of the reference sample and the sample which is currently to be calibrated are also actually coincident.

For this purpose, the following refers to FIG. 4, which basically again shows the measuring device explained by way of FIG. 2, but with an extension.

Figure 4:
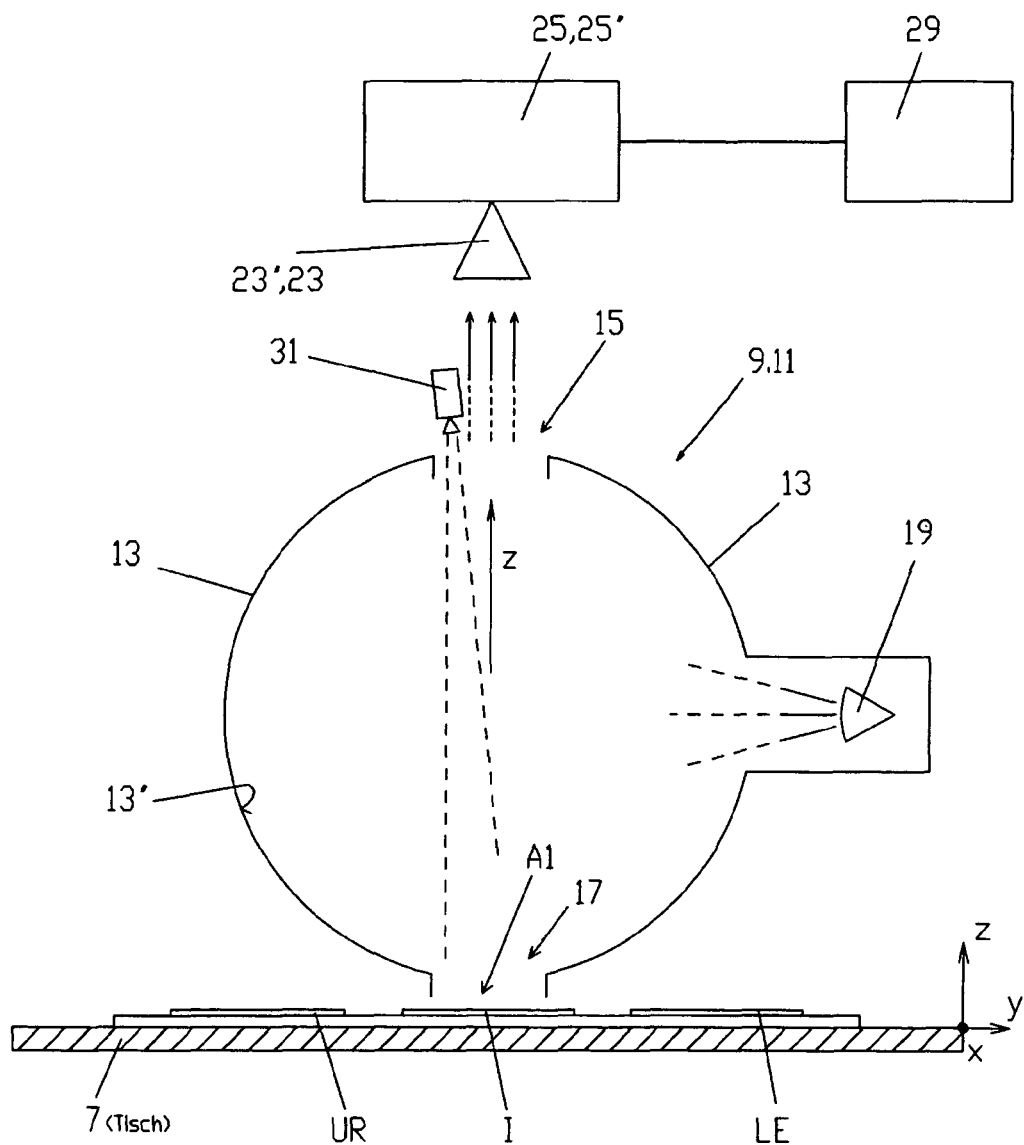
FIG. 4 is a drawing comparable to FIG. 2 with an extension in the form of a position camera.

As can be inferred from the drawing of FIG. 4, a further position detection camera 31 is provided. This camera 31 looks through the upper measuring port 15 towards the light exit port 17, positioned below, in the spherical housing 13 of the Ulbricht sphere 11. The additional camera 31 thus captures the section A1, A2 or A3 which is to be tested, which is located directly below the light exit port 17. Since this additional position detection camera 31 naturally cannot be arranged precisely in the central beam path (corresponding to the central axis positioned towards the diffraction grating and CCD camera), this additional camera 31 is positioned slightly oblique to this central axis Z. This prevents the beam path, extending to the diffraction grating, of the light reflected from the sample from being disturbed. In other words, the additional camera 31 is arranged slightly skewed, but this is irrelevant for the precise position determination of the section which is to be measured from the sample, since the small resulting parallax error, which is always present, i.e. for measuring both an original or LE sample section and an I sample section, is always the same.

The camera to be used should have a sufficiently high resolution to be able to capture even extremely fine structures of the decor which is to be tested (grains, in particular wood grains in decors, etc.).

As has already been shown by way of FIG. 1, for each decor print which is to be calibrated one or more sections A1, A2, A3 are selected and are calibrated so as to determine the beam spectrum, so as thereby to answer the question of whether or not the samples which are to be compared of this decor UR, LE and I are identical. The corresponding decor sections A1, A2 and A3, which are used for imaging optical detection and digital evaluation, may be selected in a targeted manner. The relevant decor regions which are to be tested may in this case each have a diameter of 1 cm to 5 cm, preferably from 2 cm to 3.5 cm in size. The size and the number of these decor sections which are to be tested can be set as desired.

If a sample which is newly to be tested is calibrated, the corresponding image is captured by the additionally provided position detection camera 31 (for example from a decor section A1, A2 or A3 which is to be calibrated), and simultaneously, the image previously captured from a reference section and stored is cross-faded into the decor image captured by the additional camera 31, preferably on the image screen. In other words, the data obtained in the past regarding an original sample UR or a previously printed reference sample LE are stored in the device by way of the decor section A1, A2 and/or A3 which is to be tested, for example as X-Y values, and can be called up by the spatial position and by the measurement result when a current sample is newly calibrated, and compared with the values, currently being detected by the camera, of the sample which is currently to be calibrated. This generally makes possible immediate, simple detection of whether the selected decor section of the two samples which are to be compared is fully identical (i.e. coincident) as regards the detection position thereof. This is because, in particular when evaluating decors using for example wood grains or comparable structures, "line patterns" are for example contained in the decor and are a completely typical "figure" for the decor, in such a way that if the sample which is currently to be tested is not precisely positioned, for example in relation to an original sample, corresponding wood grains or wood grain lines may possibly lie close together side-by-side. In this case, it can immediately be recognised that the two images are not yet "coincident".

From the above illustration, it follows that an exact evaluation—as to whether two decor samples are the same—is naturally only possible if precisely the same decor sections are compared with one another. For this purpose, a positioning aid is preferably provided, and makes it easier to locate the identical decor section, which corresponds to the decor section of a previously captured original sample or a most recently printed sample LE, in a decor sample which is currently to be compared.

This positioning aid may for example be implemented by an interactive method in such a way that in the respective decor section of the samples which are to be compared, a prominent point, i.e. a notable feature, is assigned a marker cross, i.e. in general a positioning cross or the like. In sections which are not yet coincident relating to the decor samples which are to be compared, a difference vector between the cross centre-points of the non-coincident position crosses can thus be determined, for example by means of the aforementioned evaluation means 29 which generally comprises a computer, and as a function thereof an automatic guiding movement of the positioning table can be implemented until the two decor samples which are to be compared are positioned absolutely identically to one another. This interactive method provides that the originally determined and fixed measuring position on an original sample or a most recently printed sample is coincident with the sample I which is to be compared.

However, instead of the aforementioned interactive method, an automatic method for achieving coincidence of the samples which are to be compared is also possible, specifically by correlating the image contents of the sample sections which are to be compared. Correlation methods of this type are based on adequate software assessment and evaluation of the sample sections which are to be compared. In this respect, software methods of this type are based on known basic methods.

Figure 5:
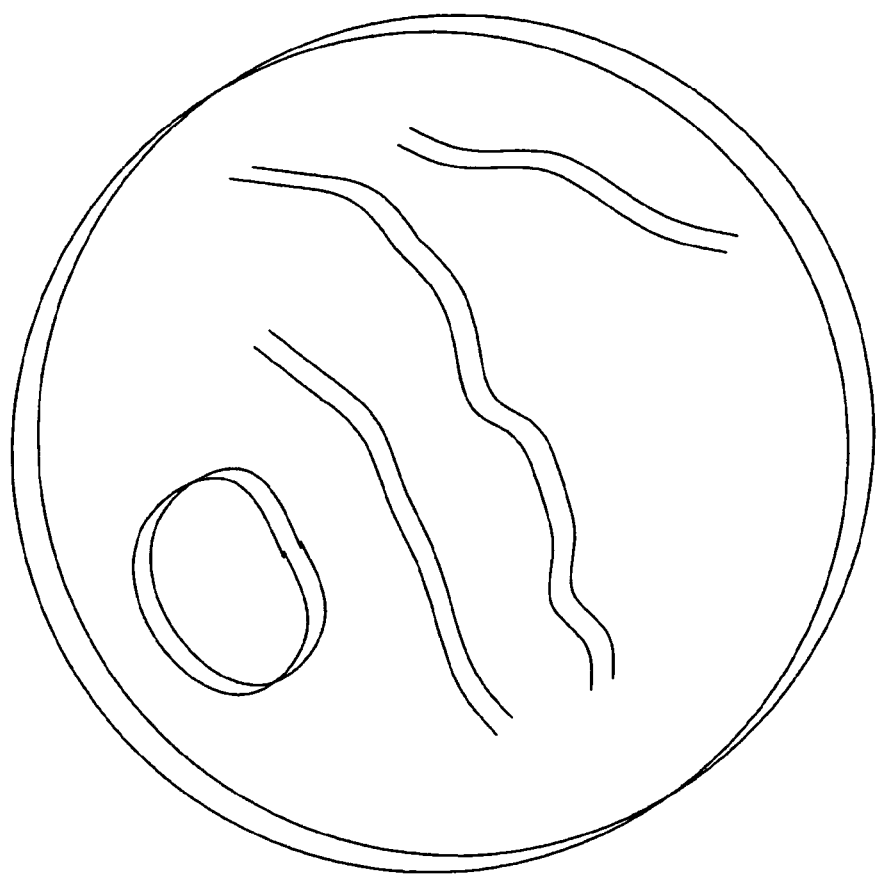
FIG. 5 shows the decor section which is to be tested with decor features identified therein in relation to a reference sample section, the two decor sections not yet having been brought into coincident alignment with one another.

FIG. 5 therefore shows an image, captured by the position detection camera 31, of a decor section A1, A2 or A3, specifically in relation both to a reference sample and to a sample which is currently to be calibrated, the relevant decor sections not yet having been made coincident in these samples. In this context, the doubling of the line structure is clear. If the coincidence between two samples which are to be compared is to be achieved manually at least in part, it is easy for an operator to displace the measuring table in the X or Y direction (or conversely to displace the measuring device above the table in a corresponding direction) until the structures located in the decor section are positioned identically on top of one another. This makes possible a definitive assertion that the decor section which is currently to be tested, for example a current actual sample I, corresponds identically to the section of an original sample or the most recently printed sample LE of the most recent delivery.

In other words, the correspondence of the respectively identical measuring points $A_1$ to $A_1$, $A_2$ to $A_2$, $A_3$ to $A_3$ etc. (sections) between the measurements on the different samples of a decor requires millimeter precision (±0.5 mm and less). In this context, the manual fine adjustment can be carried out easily based on any characteristic decor structures, such as the aforementioned grain of the wood. As stated, the easy handling is assisted by the fact that the stored and the present image data of the measurement locations (decor sections) are laid on top of one another, in that the images appear transparent and for example the aforementioned wood grains are left as a "frame", in such a way that it can be checked, with easy visual perception, whether or not the sections are exactly identical.

However, the position detection method for the images projected on top of one another of the decor sections to be compared can also be carried out in an automated manner, specifically by sample recognition methods which are basically known. This is generally carried out by correlation measures, which can be taken via the measurement location which is to be evaluated.

In the described embodiment, it has been assumed that the original sample, shown for example in FIG. 1, the actual sample I which is currently to be measured (which is supposed to represent an example of the new order to be printed), and the most recently printed sample LE are positioned correctly, for example glued, on a base U, in such a way that in fact the measuring device or the measuring table needs only be displaced in the X or the Y direction to compare the corresponding decor sections. If the sections are not positioned or provided exactly mutually parallel, it would similarly be possible and necessary for the measuring table and/or the measuring device to be rotated about an axis extending transverse to the plane of the sample, generally an axis of rotation perpendicular thereto, so as to position the decor sections which are to be compared identically to one another. Equally, unlike the measuring table, the entire measuring device can be displaced over the sample or decor sections which are to be calibrated, or the measuring table and the measuring device can be adjusted accordingly relative to one another.

Thus, overall the presently described device and the method applied in this context produce the surprising result that in this way a high-precision optical comparison of at least two or more samples is possible by comparing features extracted from decor sections that can be selected as desired, even if the decor sections have inherently different colouration and potentially also a structure-like grain, in particular as in wood imitations, which differ greatly from the basic colouration.

This is ultimately possible by evaluating high-resolution spectra which are determined globally by spectrum formation for a decor section which is to be evaluated. Thus, surprisingly, this integral method can be applied even if the samples exhibit inconsistencies in structure and colour as mentioned above. Thus, the decor sections (measuring points) in the samples can be selected in any number.

The identity of the locations at which the features of the sections which are to be compared are captured is the basis of a meaningful feature comparison. For this purpose, the described capture of a camera image of the selected section A1, A2 or A3 etc. and the comparison of this camera image with the current camera image is sufficient for establishing the section at the same location in a second sample. Thus, in other words, by correlation of the relevant image contents, in a manual or automatic camera-based manner, it can be defined exactly whether the same measuring points or sections have been taken as a basis for determining the comparison to be carried out.

The identity of the sections in the samples which are to be compared can then be provided by manual positioning, assisted by the camera images or by automatic image comparison of the camera image of the selected section of the first sample with the camera image of the current section of a second sample by correlation mechanisms, in such a way that automatic coincident positioning of the section in the second sample is possible.

The described system can thus preferably be used for decors in which for example a current sample can be compared with one, two or a plurality of other samples which act as a reference value.

The invention claimed is:

1. A method for carrying out an optical comparison of first and second two dimensional samples, each of which is patterned such that the first and second samples are not evenly colored, comprising:
    illuminating a portion of the first sample with scattered light, and guiding light reflected from the portion of the first sample through an optical wavelength separating device onto an imaging camera;
    utilizing an output of the imaging camera to generate a first spectrum for the first sample that includes light amplitude values at a plurality of different wavelengths;
    generating an image of the portion of the first sample with a position detection camera;
    storing the image of the portion of the first sample with information regarding the first spectrum;
    illuminating a corresponding portion of the second sample with scattered light, and guiding light reflected from the corresponding portion of the second sample through the optical wavelength separating device onto the imaging camera, wherein the portion of the first sample and the corresponding portion of the second sample have substantially identical patterns;
    utilizing an output of the imaging camera to generate a second spectrum for the second sample that includes light amplitude values at a plurality of different wavelengths; and
    comparing the first and second spectrums, or values derived from the first and second spectrums, to determine a degree of similarity between the first and second samples.

2. The method according to claim 1, characterised in that the first spectrum for the first sample and the second spectrum for the second sample each have a resolution of between 1 nm and 20 nm.

3. The method according to claim 1, characterised in that illuminating a portion of the first sample and illuminating a corresponding portion of the second sample comprises illuminating the first and second samples with diffuse light, which is produced by means of an Ulbricht sphere.

4. The method according to claim 3, characterised in that during the illuminating steps, the portion of the first sample and the corresponding portion of the second sample are arranged directly adjacent to a light exit port of the Ulbricht sphere, a distance between the light exit port and a surface of the first and second samples being less than 20 mm.

5. The method according to claim 4, characterised in that a measuring port, via which light reflected from the first and second samples escapes the Ulbricht sphere and is introduced into the optical wavelength separating device is provided in the Ulbricht sphere diametrically opposite the light exit port.

6. The method according to claim 1, characterised in that a diffraction grating is used as the optical wavelength separating device.

7. The method according to claim 1, characterised in that a matrix or line-scan camera, is used as the imaging camera.

8. The method according to claim 1, characterised in that a digitalised interference spectrum, or values derived therefrom, are derived from an output of the imaging camera.

9. The method according to claim 1, further comprising:
    generating an image of the second sample with the position detection camera before the second spectrum is generated; and
    adjusting a position of the second sample, if necessary, before the output of the imaging camera is used to generate the second spectrum utilizing the stored image of the portion of the first sample and the generated image of the second sample such that the illuminated corresponding portion of the second sample has substantially the same pattern as the portion of the first sample.

10. The method according to claim 9, characterized in that adjusting a position of the second sample comprises:
    selecting a prominent point in the portion of the first sample and assigning a first marker cross or positioning cross to that prominent point;
    identifying the same prominent point in the image of the second sample generated with the position detection camera, and assigning a second marker cross or positioning cross to that prominent point; and
    adjusting a position of the second sample, if necessary, such that a position of the second marker cross or positioning cross in the image of the second sample is coincident with a position of the first marker cross or positioning cross in the image of the first portion of the first sample.

11. The method according to claim 9, characterised in that the step of adjusting a position of the second sample is automatically carried out using the image of the first portion of the first sample and the image of the second sample.

12. A device for carrying out an optical comparison between at least two samples, each of which is patterned such that samples are not evenly colored, the device comprising:
- a scattered light producing device that generates scattered light and that is configured to guide the scattered light onto a sample;
- an optical wavelength separating device that separates light reflected from a sample into wavelength bands;
- an imaging camera that is configured to receive light output from the optical wavelength separating device and to generate a spectrum for a sample that includes a plurality of amplitude values at a corresponding plurality of wavelength ranges;
- a positioning device that is configured to cause the scattered light producing device, the optical wavelength separating device and the imaging camera to generate a first spectrum from a first portion of a first sample, and a second spectrum from a corresponding portion of a second sample, the first portion of the first sample and the corresponding portion of the second sample having substantially identical patterns;
- an evaluation unit that is configured to determine a degree of similarity between the first and second samples based on the spectrums generated for the first portion of the first sample and the corresponding portion of the second sample, or values derived from the spectrums generated for the first and second samples; and
- a position detection camera that is configured to generate an image of a portion of a sample, wherein a generated image of a portion of a sample is stored along with a spectrum generated for the sample.

13. The device according to claim 12, wherein the optical wavelength separating device and the imaging camera are configured to generate a spectrum for a sample having a resolution of between 1 nm and 20 nm.

14. The device according to claim 12, wherein the scattered light producing device comprises an Ulbricht sphere.

15. The device according to claim 14, characterised in that a sample which is to be analysed is arranged directly adjacent to a light exit port of the Ulbricht sphere, a distance between the light exit port and the surface of the sample being less than 20 mm.

16. The device according to claim 15, characterised in that a measuring port, via which light reflected from a sample is guided to the optical wavelength separating device, is provided in the Ulbricht sphere diametrically opposite the light exit port.

17. The device according to claim 12, wherein the optical wavelength separating device comprises a diffraction grating.

18. The device according to claim 12, wherein the imaging camera comprises a matrix or line-scan camera.

19. The device according to claim 12, wherein the evaluation unit is configured to generate a digitalised interference spectrum, or values derived therefrom, based on an output of the imaging camera, and wherein the evaluation unit utilizes digitalized interference spectrums, or values derived therefrom, from two samples to determine a degree of similarity between the two samples.

20. The device according to claim 12, wherein the positioning device is configured to adjust a position of a second sample, based on a stored image of a portion of a first sample, such that a pattern of an analyzed portion of the second sample substantially matches a pattern of the stored image of the portion of first sample.

21. The device according to claim 20, wherein the positioning device identifies a prominent point in a first image of a portion of a first sample generated by the position detection camera and assigns a marker cross or positioning cross to that prominent point, wherein the positioning device identifies the same prominent point in a second image of a portion of a second sample generated by the position detection camera, and wherein the positioning device adjusts a position of the second sample until the positioning or marker crosses of the first and second images are coincident.

22. The device according to claim 12, characterised in that the positioning device is configured to automatically adjust a position of a second sample based on images of first and second samples generated by the position detection camera such that an analyzed portion of the second sample has substantially the same pattern as an analyzed portion of the first sample.

* * * * *